(12) United States Patent
Pignol et al.

(10) Patent No.: US 7,696,197 B2
(45) Date of Patent: Apr. 13, 2010

(54) USE OF A PHENOTHIAZINE DERIVATIVE FOR PREVENTING AND/OR TREATING HEARING LOSS

(75) Inventors: Bernadette Pignol, Paris (FR); Jean-Luc Puel, Cournonterral (FR); Serge Auvin, Palaiseau (FR); Pierre-Entienne Chabrier de Lassauniere, Paris (FR); Jing Wang, Lunel (FR)

(73) Assignee: Societe de Conseils de Recherches et d'Applications Scientifiques, Paris (FR)

( * ) Notice: Subject to any disclaimer, the term of this patent is extended or adjusted under 35 U.S.C. 154(b) by 444 days.

(21) Appl. No.: 10/594,960

(22) PCT Filed: Mar. 25, 2005

(86) PCT No.: PCT/FR2005/000713

§ 371 (c)(1),
(2), (4) Date: Sep. 29, 2006

(87) PCT Pub. No.: WO2005/092345

PCT Pub. Date: Oct. 6, 2005

(65) Prior Publication Data

US 2008/0275034 A1    Nov. 6, 2008

(30) Foreign Application Priority Data

Mar. 29, 2004  (FR) .................................. 04 03203
Jun. 14, 2004  (FR) .................................. 04 06404

(51) Int. Cl.
A61K 31/54   (2006.01)
A01N 43/08   (2006.01)
A61K 31/34   (2006.01)

(52) U.S. Cl. .................................. 514/224.8; 514/461
(58) Field of Classification Search ............... 514/224.8
See application file for complete search history.

(56) References Cited

FOREIGN PATENT DOCUMENTS

WO   WO 01/32654    5/2001
WO   WO 02/40016    5/2002
WO   WO 2005/056551  6/2005

OTHER PUBLICATIONS

Takumida, Masaya et al.: "Neuroprotection of vestibular sensory cells from gentamicin ototoxicity obtained using nitric oxide synthase inhibitors, reactive oxygen species scavengers, brain-derived neurotrophic factors and calpain inhibitors." Acta Oto-Laryngologica. Jan. 2003, vol. 123, No. 1, pp. 8-13—XP008038195.
Wang, Jing et al.: "Leupeptin protects sensory hair cells from acoustic trauma." Neuroreport, vol. 10, No. 4, Mar. 17, 1999, pp. 811-816, XP008038205.
Franze, Annamaria et al.: "Effect over time of allopurinol on noise-induced hearing loss in guinea pigs." International Journal of Audiology, vol. 42, No. 4, Jun. 2003, pp. 227-234, XP008038194.
Seidman, M.D.: "Effects of dietary restriction and antioxidants on presbyacusis." Laryngoscope 2000 United States, vol. 110, No. 5 I, 2000, pp. 727-738, XP008038200.
Pignol, B. (Reprint) et al.: "Doxorubicin (Doxo) induced muscle wasting of mice. Protective effect of BN82270, a hybrid molecule with dual activity (alpain inhibitor and antioxidant) on cachexia." Neuromuscular Disorders, Sep. 2004, vol. 14, No. 8-9, p. 611, XP002337502.
Auvin, Serge et al.: "Novel dual inhibitors of calpain and lipid peroxidation." Bioorganic & Medicinal Chemistry Letters, vol. 14, No. 14, Jul. 16, 2004, pp. 3825-3828, XP002304686.
Yamashita, D. et al.: "Delayed production of free radicals following noise exposure." Brain Research Sep. 3, 2004, Netherlands, vol. 1019, No. 1-2, pp. 201-209, XP0080038192.

*Primary Examiner*—San-ming Hui
*Assistant Examiner*—Paul Zarek
(74) *Attorney, Agent, or Firm*—Hunton & Williams LLP (57) ABSTRACT

The invention concerns the use of a phenothiazine derivative of formula (I), wherein: R represents the hydrogen atom, an alkyl radical, arylalkyl, or —C(O)R', for preparing a medicine for preventing and/or treating hearing loss.

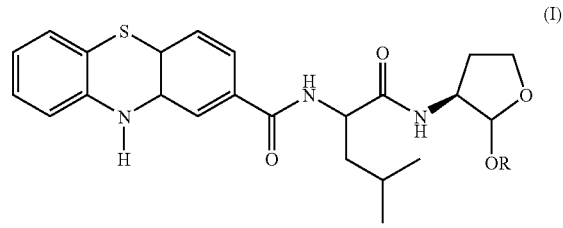

31 Claims, 4 Drawing Sheets

USE OF A PHENOTHIAZINE DERIVATIVE FOR PREVENTING AND/OR TREATING HEARING LOSS

CROSS-REFERENCE TO RELATED APPLICATIONS

This application claims the benefit and is the U.S. National Stage Entry of International Patent Application No. PCT/FR2000/000713, filed Mar. 25, 2005, which claims priority to FR0403203, filed Mar. 29, 2004 and FR0406404, filed Jun. 14, 2004, the disclosures of each of which are herein incorporated by reference in their entirety.

FIELD OF INVENTION

The present invention relates to the use of a phenothiazine derivative having a calpain inhibiting activity and an activity which traps the reactive oxygen species (ROS) for the preparation of a medicament intended to prevent and/or treat hearing loss. The invention also relates to a product comprising at least one such compound and a pharmaceutical composition containing it.

BACKGROUND OF INVENTION

Among the many causes of hearing loss, there may be mentioned in particular diseases such as meningitis or otitis, genetic causes, injuries, tumours, drugs, the administration of medicaments such as certain antibiotics, anti-cancer drugs, non-steroidal anti-inflammatory agents, diuretics, ulcer drugs or anticonvulsants, prolonged exposure to aromatic organic solvents such as toluene or xylene, ageing and exposure to noise. Presbycusis (age-related deafness), prolonged exposure to noise and the administration of medicaments are the main causes of hearing loss.

Today it is well known that certain antibiotics of the aminoglycoside family, such as gentamicin and tobramycin, which are used in the treatment of serious infections are responsible for cochlear deafness. The toxicity to aminosides (aminoglucosides such as amikacin, dibekacin, gentamicin, isepamicin, netilmicin, spectinomycin, tobramycin) initially expresses itself by an impairment of hearing at high frequencies and is not at first recognized by the patient. The latter will only gradually be bothered by this. Unfortunately it is often irreversible.

The noise around us lowers our hearing ability. Hearing loss caused by noise occurs when the acoustic hair cells which convey sound towards the inner ear are damaged and can no longer order the auditory nerve to send electrical pulses to the brain.

The volume of the sound and the duration of exposure are the two main factors influencing hearing loss. Although the reaction to exposure to noise varies from one person to the next, some facts can be reported with certainty. Research has shown that prolonged exposure to 85 decibels (dB) or more will, over time, cause permanent hearing loss.

European and North American statistics show that 8 to 10% of the population suffer from cochlear pathologies (deafness, tinnitus). Given the sound levels produced in discotheques, techno concerts and also by walkmans, a whole generation of deaf people and tinnitus sufferers is being created. Thus age-related problems (presbycusis) which these days start at around 60 years of age, could start much earlier, i.e. around 35-40 years of age.

The problem with auditory pathologies is that the great majority of them result from the loss of the acoustic hair cells and nerve cells of the inner ear (or cochlea). These cells, beyond a development phase which is essentially intra-uterine, do not have the ability to renew themselves after their last stage of differentiation.

The progressive loss of the sensitive and nervous powers of the ear related to different cochlear pathologies even today still appears to be beyond the scope of any treatment.

DETAILED DESCRIPTION OF THE INVENTION

The subject of the invention is therefore the use of a heterocyclic derivative which corresponds to the formula (I)

in the form of diastereoisomers or any combinations of these forms, in which R represents the hydrogen atom, a $(C_1-C_6)$ alkyl, arylalkyl or —C(O)R' radical in which R' represents a heterocycloalkyl, $(C_1-C_6)$ alkyl, aryl or aralkyl radical;

the alkyl, aryl or heterocycloalkyl radicals being optionally substituted by one or more identical or different substituants chosen from: $(C_1-C_6)$ alkyl, hydroxy, $(C_1-C_6)$ alkoxy, nitro, cyano, halogen or —NR$_1$R$_2$;

R₁ and R₂ represent, independently, a hydrogen atom or an (C₁-C₆)alkyl radical, or R₁ and R₂ form together with the nitrogen atom to which they are attached an optionally substituted heterocycle,
for the preparation of a medicament intended to prevent and/or treat hearing loss.

In the present application, by "traumatism" is meant a group of local lesions involving the tissues and organs, caused by an external agent. In the case of acoustic traumatism, the external agent is mainly noise.

By (C₁-C₆)alkyl is meant a linear or branched alkyl radical containing from 1 to 6 carbon atoms such as, for example, the methyl, ethyl, propyl, isopropyl, butyl, isobutyl, sec-butyl and tert-butyl, pentyl, neopentyl, isopentyl, hexyl, isohexyl radicals. The (C₁-C₆)alkoxy radicals can correspond to the alkyl radicals mentioned above such as for example the methoxy, ethoxy, propyloxy or isopropyloxy radicals but also linear, secondary or tertiary butoxy. The alkylcarbonyl radicals can correspond to the alkyl radicals mentioned above such as for example the methylcarbonyl, ethylcarbonyl, propylcarbonyl. By halogen is meant the fluorine, chlorine, bromine, or iodine atoms.

By aryl is meant a carbocyclic or heterocyclic system comprising at least one aromatic ring, a system being called heterocyclic when at least one of the rings of which it is composed comprises a heteroatom (O, N or S). As an example of a carbocyclic aryl radical, phenyl or naphthyl can be mentioned. As an example of a heterocyclic aryl (or heteroaryl) radical, thienyl, furyl, pyrrolyl, imidazolyl, pyrazolyl, isothiazolyl, thiazolyl, isoxazolyl, oxazolyl, pyridyl, pyrazinyl, pyrimidyl, benzothienyl, benzofuryl and indolyl can be mentioned.

The term heterocycle (or heterocycloalkyl), preferably represents a mono- or bicyclic heterocycle, saturated or unsaturated, comprising from 1 to 5 heteroatoms chosen from O, S and N. The nitrogen atom can optionally be substituted by a radical chosen from: alkyl, aryl, aralkyl and alkylcarbonyl. As an example of a saturated heterocycle, there can be mentioned: tetrahydrofuran, tetrahydropyran, oxetane, oxepane, tetrahydrothiophene, tetrahydrothiopyran, thietane, pyrrolidine, piperidine, azetidine, 1,3-dioxane, 1,3-dioxolane, 1,3-dithiolane, 1,3-dithiane, 1,3-oxathiolane, 1,3-oxazolidine, 1,3-imidazolidine or 1,3-thiazolidine. As an example of an unsaturated heterocycle, there may be mentioned: dihydrothiophene, dihydrofuran, dihydropyrrole, dihydroimidazole, dihyropyrazole, dihydropyridine, indoline.

The arylalkyl (or aralkyl) radicals designate the radicals in which respectively the aryl and alkyl radicals are as defined above such as for example benzyl, phenethyl or naphthylmethyl.

In the case of the radical of formula —NR₁R₂ where R₁ and R₂ form together with the nitrogen atom to which they are attached an optionally substituted heterocycle, the heterocycle is preferably saturated and comprises from 4 to 7 members and from 1 to 3 heteroatoms including the nitrogen atom already present, the additional heteroatoms being chosen independently from the group constituted by the O, N and S atoms. Said heterocycle can be, for example, the azetidine, pyrrolidine, piperidine, piperazine, morpholine or thiomorpholine ring. Said heterocycle can be substituted by one or more identical or different substituents chosen from the hydroxy group, an alkyl, aryl, aralkyl or alkoxy radical or a halogen atom.

More particularly a subject of the invention is a use as defined above, characterized in that R represents —C(O)R' and preferably R' represents an alkyl radical.

Very preferably, the compound (I) is characterized in that R represents —C(O)—CH₃.

The latter compound will hereafter be known as compound (1).

More particularly a subject of the invention is a use as defined above, characterized in that R represents hydrogen.

Also very preferably, the compound (1) as defined above has the formula (I_A)

and more particularly one of the following formula (I_A1)

(I_A2)

Also very preferably, the compound (1) as defined above has the formula (I_B)

and more particularly (I_B1)

(I<sub>B2</sub>)

The compounds as defined above are protective agents combining antioxidizing and anti-calpain effects and described in the application WO 01/32654.

A subject of the present invention is therefore also a use of a compound of formula (I) as defined above, in pre- or post-treatment relating to the origin of the hearing loss.

A subject of the present invention is also a use of a compound of formula (I) as defined above, for the preparation of a medicament intended to prevent and/or treat hearing loss following the administration of another medicament. Preferably, the other medicament is an antibiotic such as gentamicin, an anti-cancer drug such as cisplatin, a non-steroidal anti-inflammatory agent such as derivatives of salicylic acid or ibuprofen, a diuretic such as furosemide, an antiulcerative such as cimetidine or omeprazole, an anticonvulsant agent such as carbamazepine or valproic acid. Very preferably, the other medicament is an antibiotic agent and more particularly gentamicin.

A subject of the present invention is also a use of a compound of formula (I) as defined above, for the preparation of a medicament intended to prevent and/or treat hearing loss following presbycusis.

A subject of the present invention is also a use of a compound of formula (I) as defined above, for the preparation of a medicament intended to prevent and/or treat hearing loss following an acoustic traumatism.

The compounds according to the invention can be used alone or in combination with at least one other substance with pharmaceutical activity and preferably a substance which is able to prevent and/or treat hearing loss or to prevent and/or treat any pathologies associated with hearing loss.

The compounds can be combined with antioxidants, calpain inhibitors such as leupeptin or Neurodur, peripheral vasodilitators such as EGb 761®, agonists or antagonists of the NMDA receptor, peptide inhibitors of c-Jun N-terminal kinase such as D-JNK-1.

A subject of the invention is also the use as defined above, characterized in that it is combined with at least one other substance with pharmaceutical activity, and preferably with a substance chosen from: antioxidants, calpain inhibitors, peripheral vasodilitators, agonists or antagonists of the NMDA receptor, peptide inhibitors of c-Jun N-terminal kinase.

A compound of formula (I) and preferably the compound (1) as defined above, can be administered at a dose comprised between 50 to 500 μM as a local application. In the case of a local intracochlear treatment, it can be administered at a dose comprised between 50 and 200 μM. In the case of a local extracochlear treatment, it can be administered at a dose comprised between 200 and 500 μM. The substances which are optionally combined with them, known in pharmacology, are administered at the normally recommended doses.

The compounds as defined above as well as the substances with pharmaceutical activity which are optionally combined with them, can be administered by the standard administration routes such as oral, intraperitoneal, subcutaneous or intravenous. They can be administered simultaneously or separately, via the same or different administration routes. Preferably, the compound (I) as defined above is administered locally by techniques commonly used in the treatment of the inner ear such as microcatheters, syringes for transtympanic injection or tubes equipped with a wick of the Silverstein Microwick type.

A subject of the invention is also a product comprising the heterocyclic derivative of formula (I) as defined above, in the form of diastereoisomers or any combinations of these forms, and at least one substance with therapeutic activity, as a combination product for a use which is simultaneous, separate or spread over time in order to prevent and/or treat hearing loss. Preferably, a subject of the invention is a product as defined above, to prevent and/or treat hearing loss, either after the administration of a medicament, or after presbycusis, or after an acoustic traumatism.

Finally a subject of the invention is, as a medicament, a product as defined above.

In the case of hearing loss after the administration of a medicament, the latter is preferably an antibiotic, and preferably gentamicin.

The substances with pharmaceutical activity with which it is optionally combined are administered via the administration routes usually envisaged for these substances in the therapeutic field considered.

In the case of hearing loss caused by an acoustic traumatism, the administration of a compound (I) as defined above, can occur a few days before the acoustic traumatism preferably 2 to 3 days before the traumatism, and 24 hours after the traumatism. Preferably, this administration occurs in the 7 days following the traumatism. Preferably also, this administration can occur in the 2 hours following the traumatism.

A subject of the invention is therefore the use described above, characterized in that the compound (1), in the form of diastereoisomers or any combination of these forms, is administered in the 7 hours and preferably in the hour following the traumatism.

The results showing the therapeutic effectiveness of compound (1) on functional recovery after acoustic traumatism are presented in the experimental part.

The following examples are presented in order to illustrate the above procedures and should in no event be considered to be a limit to the scope of the invention.

EXPERIMENTAL PART

Pharmacological Study

1) Ototoxicity Induced by a Treatment with Gentamicin
   Demonstration of the protective effect of compound 1, administered as a co-treatment, vis-à-vis the acoustic hair cell loss induced by gentamicin.

Gentamicin and other aminoglycosides have been shown to cause damage to the acoustic hair cells and hearing loss in humans. Zebrafish display the sensory organs on the surface of their bodies, called neuromasts. In these fish, the neuromast acoustic hair cells can be stained with DASPEI and this staining reflects the number of acoustic hair cells. These acoustic hair cells are structurally and functionally similar to the internal acoustic hair cells of the human ear.

Damage to the internal acoustic hair cells is induced in zebrafish by gentamicin. In order to test the effect of compound (1) on the protection of the acoustic hair cells damaged by gentamicin, the compound (1) was administered as a co-treatment with gentamicin. The internal acoustic hair cells are then stained and quantified.

The study is undertaken on fish aged 5 days incubated with 1 μg/ml of gentamicin for 24 hours in the presence or in the absence of compound (1). Controls are carried out in parallel; single vehicle (1% DMSO; positive control). The fish treated with gentamicin are the negative controls.

DASPEI (2,4-dimethyl-aminostyryl-N-ethyl pyridinium iodide) staining is carried out in order to visualize the acoustic hair cells in vivo (n=5 per group). Morphometric analysis is used in order to quantify the staining signal of the acoustic hair cells. The signal for DASPEI staining of the positive controls was defined as 100%.

Figure 1:
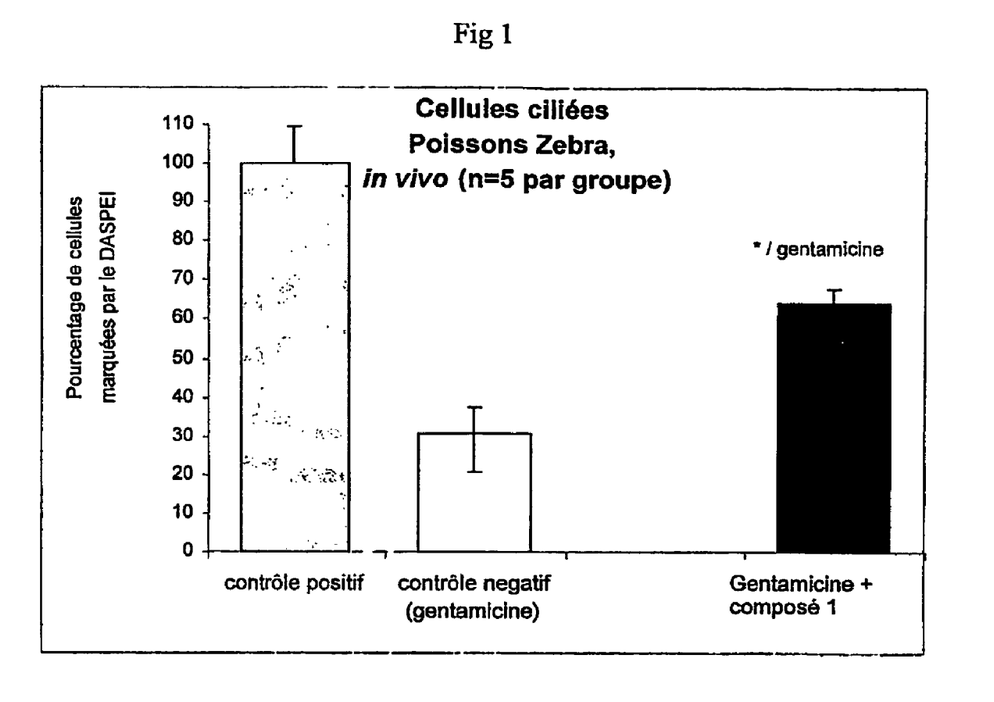
FIG. 1 depicts a graph of the percentage of cells stained in fish of compound (1) in relation to positive and negative controls.

The results are presented in FIG. 1 (Percentage of acoustic hair cells stained with DASPEI. Positive control (zebra-1% DMSO); negative control (zebra-1% DMSO-gentamicin 1 μg/ml) and effect of the product (zebra-1% DMSO-gentamicin-compound 1). Experiment carried out on 5 animals per group).

The results of FIG. 1 show that:
the staining signal of the negative control represents 31.5±4.2% of the control signal, or a loss of 68.5±4.9% of the acoustic hair cells following treatment with gentamicin.
the staining signal of the animals treated with gentamicin and the compound 1 represents 65.2±4.4% of the control signal or a very significant protection of 48.7±2.63% of the damaged acoustic hair cells by treatment with gentamicin.

2) Hearing Loss after an Acoustic Trauma

This involves the study in guinea pigs of the protective effects of the compound (1) in pre- and post-treatment on the protection of the acoustic hair cells of the inner ear on the one hand and the functional recovery of hearing on the other hand, following hearing loss caused by an acoustic trauma. The compound (1) was administered by local route "intra- and extracochlear" so as to simulate its use in surgical clinical medicine for humans.

The functional recovery obtained with this novel protective agent is quantified using a functional test which is the reading of the audiogram of the animals. This audiogram is produced by recording the activity of the potential composite action of the auditory nerve. The audiograms are recorded before and after the acoustic traumatism. Analyses by scanning electron microscopy complete this functional data by a study of the cell loss along the cochlear spiral as well as the protective effect of compound (1).

All the experiments are carried out on guinea pigs; each experiment is carried out according to a similar schema.

Figure 2:
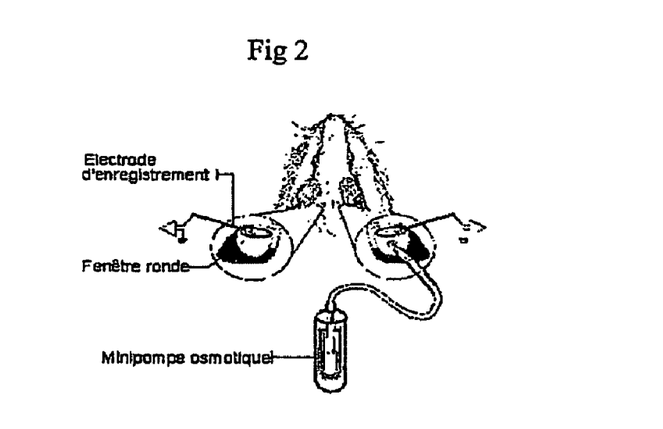
FIG. 2 depicts the placement of electrodes around an osmotic minipump used for the administration of compound (1).

The general schema of an experimental phase is as follows:
the animals are anaesthetized with an intramuscular injection of a mixture of Rompun® at 2% (3 mg/kg)+Zoletil® (40 mg/kg). This anaesthesia has the advantage of rapid dissipation and can be maintained for several hours by the regular injection (every 2 hours) of a third of the initial dose.
the placement of the electrodes and of the minipump according to FIG. 2.

The cochlear is approached by a dorsal access. After having shaved and cleaned the scalp, an incision of 2 cm is made behind the auricle. The parotid and the muscular planes covering the tympanic bulla are reclined. Once dried and cleaned, the bone is pierced in its upper wall below where the facial nerve emerges. The active electrode (platinum wire with a diameter of 0.13 mm, sheathed with Teflon) is then introduced into the bulla and placed in contact with the membrane of the round window under the control of an operating microscope (WILD M650). After recording the metric hearing thresholds, a small hole of 0.2 mm in diameter is manually countersunk in the basal turn of the tympanic canal just beneath the round window.

A glass pipette (0.1 mm in diameter at the tip), connected to the micropump via a catheter, is inserted into the cochlea using a second micromanipulator. The tympanic bulla, including the recording electrode and the perfusion pipette, is closed with dental resin.

The micropump is slid beneath the skin of the animal, the muscular and cutaneous planes are swabbed with betadine, sutured with absorbable sutures and covered with an antibiotic solution (Rifocin 5P100®).

A second incision of approximately 1.5 cm is then made on the vertex with a view to fixing a connector (Connectral, ref.: 8/45-05.050.000) on the skull of the animal. After having scraped the periosteum of the bone, this area is carefully dried, swabbed with silver nitrate then covered with a film of cyanolite.

The (active and reference) electrodes are slid beneath the skin to the connector to which they are welded. The connector is then fixed on the skull with dental resin.

Stimulation Techniques:

The sound stimulations are produced using two Hewlett Packard synthesizers (HP 3314 A and HP 8904 A) and delivered in free field by means of a loudspeaker (JBL 075) placed 10 cm from the ear. The calibration of the acoustical system is carried out in an artificial ear using a ½-inch microphone (type 4134, Bruel and Kjaer) and a measuring amplifier (type 2606) allowing direct reading of the sound level in decibels SPL (dB SPL, reference: 2.10-5 Pa). In order to display the acoustic signals, the output of the measuring amplifier is connected to an oscilloscope. The animals are exposed to a sound of 6 kHz, at 120 dB SPL for 30 minutes.

Recording Techniques:

The cochlear responses recorded by the electrode implanted in the cochlea via the connector fixed on the head of the animal are amplified (gain 1000) and filtered (32 Hz-3200 Hz) using a preamplifier and a differential amplifier of the GRASS P 511 K type. The direct trace is displayed on an oscilloscope (Tektronix type 513). This signal is averaged (256 passes) to reduce the background noise, and stored on a 486 PC computer, 66 megahertz (Hewlett-Packard-Vectra 05/65). The threshold criterion is defined as being the value in dB SPL necessary to produce a measurable response (>2 μV). Two electrodes placed in contact with the cochlea (round window) allow recording of the cochlear responses and production of audiograms for each ear. The metric audio thresholds are recorded 20 minutes after the sound traumatism and every day for one month.

Involvement of the Activation of Calpain after an Acoustic Trauma:

The cleavage of a specific substrate of calpain, fodrin, is quantified in order to determine the activation of the calpain enzyme after an acoustic trauma. Calpain cleaves the 240 KD fodrin to form a 150 KD degradation product. A double marking is carried out with a polyclonal antibody specific to the 150 KD fragment and an anti-calbindin antibody allowing identification of the acoustic hair cells. The fluorescence is displayed with a confocal microscope.

Molecular Mechanisms of the Death of Acoustic Hair Cells after an Acoustic Trauma:

In order to determine the nature of cell death, the fragmentation of the DNA of the cochlear cells is quantified using the TUNEL method.

Determination of the Integrity of the Acoustic Hair Cells after an Acoustic Trauma The integrity of the cochlear cells is determined by immunocytochemistry using an anti-cytochrome C antibody. In healthy cells, the cytochrome C is localized in the mitochondria. After an acoustic trauma, the cytochrome C is diffused and distributed in the cytoplasm.

Phase 1: Demonstration of the Protective Effect of Compound (1), Administered as a Pre-Treatment, Vis-à-Vis the Hearing Loss and Cell Loss Along the Cochlear Spiral Caused by the Traumatism Protocol—Phase 1: Pre-Administration of Compound (1)

An osmotic minipump, placed under the skin, delivers the compound (1).

The animals undergo the sound traumatism inside the cochlea via a catheter (intracochlear infusion), two days after the implantation of the minipump.

This experiment is carried out on 7 animals then 30 animals for the dose-response.

The compound (1) is applied directly into the cochlea (intracochlear perfusion) via an osmotic minipump (flow rate of 1 µl/h, 200 µl volume, diffusion duration 7 days) permanently implanted in the cochlea 2 days before the traumatism. This technique allows determination of the protective effect of compound (1), at a dose of 100 µM, vis-à-vis the cell loss along the cochlear spiral caused by the traumatism as well as the functional recovery of hearing. Then a dose effect of the product allows determination of the effective dose allowing 50% of hearing to be preserved.

Results Phase 1

The compound (1) at a concentration of 100 µM.

Functional Test Measured by Audiogram. Hearing Loss after an Acoustic Trauma and Protection with Compound 1.

Figure 3:
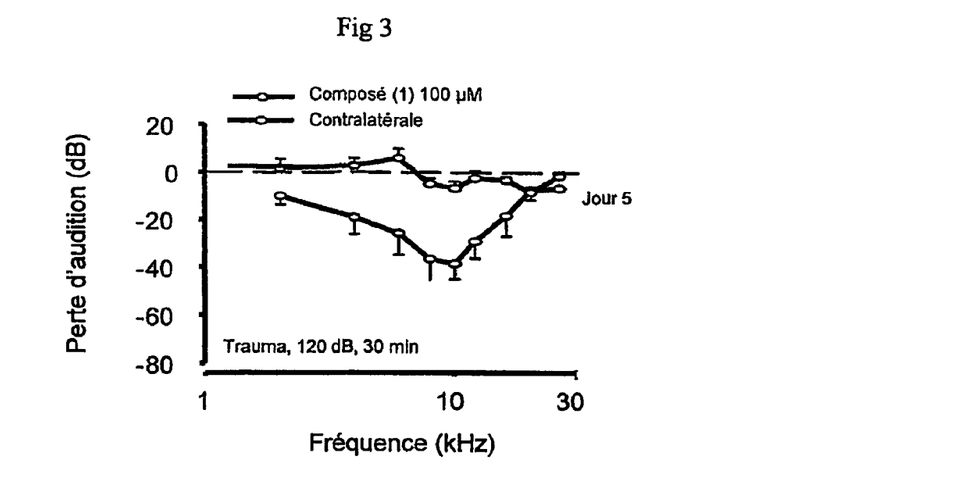
FIG. 3 depicts a graph of hearing loss with respect to frequency after acoustic trauma and protection with compound (1).

Five days after a traumatism of 120 dB for a period of 30 min, the reading of the audiograms allows the effectiveness of compound (1) to be demonstrated; this product allows recovery of 100% of hearing (FIG. 3) when it is perfused at 100 µM, 2 days before this traumatism.

Morphological Study: Histology of the Cells Along the Cochlear Spiral after an Acoustic Trauma. Protection with Compound (1).

At the end of the electrophysiological evaluation (audiogram), 30 days after the acoustic trauma, the cochlea of the animals are sampled, and prepared for electron microscopy.

The cell loss is determined by counting the ciliary tufts with a scanning microscope. Qualitative data is sought by undertaking highly magnified observations of the surface of the organs of Corti.

Figure 4:
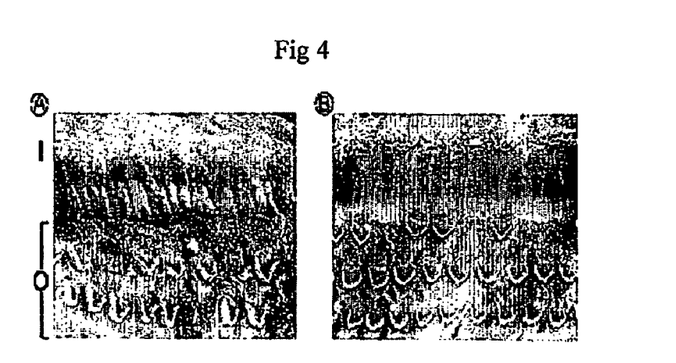
FIG. 4 depicts Histiological data of acoustic trauma (A) and compound (1) and acoustic trauma (B).

After a traumatism of 120 dB for a duration of 30 min, the internal acoustic hair cells are destroyed as well as some of the three rows of external acoustic hair cells. The histology of these cells allows the effectiveness of compound (1) to be demonstrated. This product allows 100% of the internal acoustic hair cells and a large part of the external acoustic hair cells to be protected when it is perfused at 100 µM, 2 days before this traumatism (FIG. 4: Histological data; Photo A: acoustic trauma; Photo B: compound (1)+acoustic trauma; I=internal acoustic hair cells; O=external acoustic hair cells).

Involvement of the Activation of Calpain after an Acoustic Trauma. Inhibition with Compound 1.

The activation of the calpain enzyme is determined by the quantification of the degradation of a specific substrate of the enzyme, fodrin, to a 150 KD fragment.

This cleavage of fodrin is never detected in the cochlear cells in controls.

Figure 5:
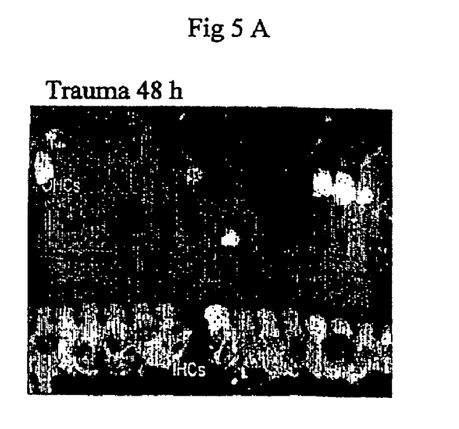
FIG. 5A depicts Fodrin Breakdown products 48 hours after acoustic trauma.
FIG. 5B depicts Fodrin Breakdown products 48 hours after acoustic trauma and application of compound (1).

After an acoustic trauma, the immunomarking of the 150 KD fragment, originating from the cleavage of fodrin due to the activation of the calpain enzyme, is visible on the external cochlear cells due to marking with the anti-FBDP antibody ("Fodrin Breakdown products", green fluorescence; FIG. 5 A: 48 hours after the acoustic trauma). This activation of the calpain activity after an acoustic trauma is related to a loss of the cells of the cochlea visualized by the absence of marking by the anti-calbindin antibody which allows identification of the intact acoustic hair cells.

The local application of 100 µM of compound (1), a calpain activation inhibitor antioxidant, prevents the cleavage of fodrin by the calpain enzyme in the cochlear cells exposed to an acoustic trauma. This absence of green fluorescent marking, thus of the non-degradation of the specific substrate of calpain is related to a protection of the cochlear cells (marking with anti-calbindin antibodies; FIG. 5 B).

Molecular Mechanisms of the Death of Acoustic Hair Cells after an Acoustic Trauma. Protection with Compound 1.

In order to determine the nature of the death of the cochlear cells caused by an acoustic trauma, the fragmentation of the DNA (quantified by the TUNEL method) is carried out on animals which have undergone an acoustic trauma. The effect of compound 1 is tested on this parameter in order to determine its involvement via this mechanism of cell death by apoptosis.

No "TUNEL-positive" cells are observed in the cochlea obtained from the control animals not exposed to noise.

Figure 6:
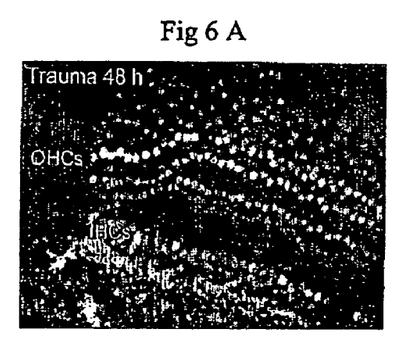
FIG. 6A depicts fragmentation of DNA quantified by the TUNEL method 48 hours after acoustic trauma.
FIG. 6B depicts fragmentation of DNA quantified by the TUNEL method 48 hours after acoustic trauma and application of compound (1).

The cochlea exposed to an acoustic trauma have TUNEL-positive cell nuclei in the region of the organ of Corti (FIG. 6A: 48 hours after the acoustic trauma). The marked nuclei are localized in the upper region of the organ of Corti. It is therefore likely that these marked nuclei belong to the acoustic hair cells rather than to the support cells. Many marked nuclei are visible one hour after the acoustic trauma and this marking is still visible 4 days after the acoustic trauma. The cell death of the acoustic hair cells after an acoustic trauma is therefore obtained via an apoptotic mechanism related to a fragmentation of the DNA.

The local application of 100 µM of compound (1), a calpain activation inhibitor and antioxidant, prevents the marking of the nuclei of the acoustic hair cells (TUNEL method, FIG. 6B: compound (1)-48 hours after the acoustic trauma). Compound (1) suppresses cell death by apoptosis caused by an acoustic trauma.

Loss of the Integrity of the Acoustic Hair Cells after an Acoustic Trauma. Protection with Compound (1).

In order to determine the loss of integrity of the acoustic hair cells after an acoustic trauma, the diffusion of the cytochrome C by immunocytochemistry via the use of an anti-cytochrome C antibody is carried out on animals which have undergone an acoustic trauma.

Compound (1) is tested on the release of cytochrome C, from the mitochondrial compartment to the cytoplasmic compartment, in order to determine its effect on the loss of integrity of the acoustic hair cells after an acoustic trauma.

In the cochlea obtained from the control animals not exposed to noise, the cytochrome C is localized in the mitochondria.

Figure 7:
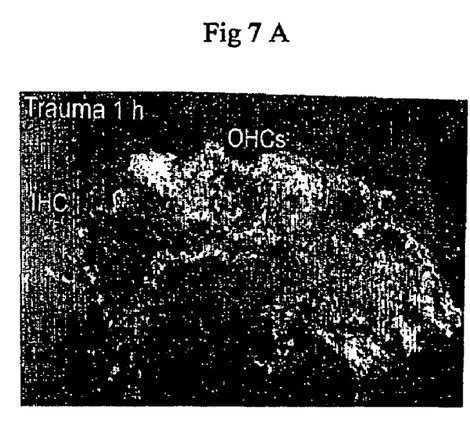
FIG. 7A depicts the release of Cytochrome C into cytoplasm 1 hour after acoustic trauma.
FIG. 7B depicts the release of Cytochrome C into cytoplasm 1 hour after acoustic trauma and application of compound (1).

The cochlea exposed to an acoustic trauma show a marking of cytochrome C which is diffused and distributed in the cytoplasm (FIG. 7A).

The local application of 100 µM of compound (1), a calpain activation inhibitor and antioxidant, prevents the dispersion of cytochrome C from the mitochondria towards the cytoplasm of the acoustic hair cells exposed to the acoustic trauma and thus maintains the integrity of the cells (FIG. 7B).

Dose-response Curve of Compound (1).

The protective effect of compound (1) was evaluated by varying the dose in order to define the effective dose allowing to recover 50% of the hearing lost ($ED_{50}$). Eight groups of 5 animals including those receiving artificial perilymph only and those receiving 1, 3, 10, 33, 100 µM of compound (1), i.e. 30 animals are used.

Figure 8:
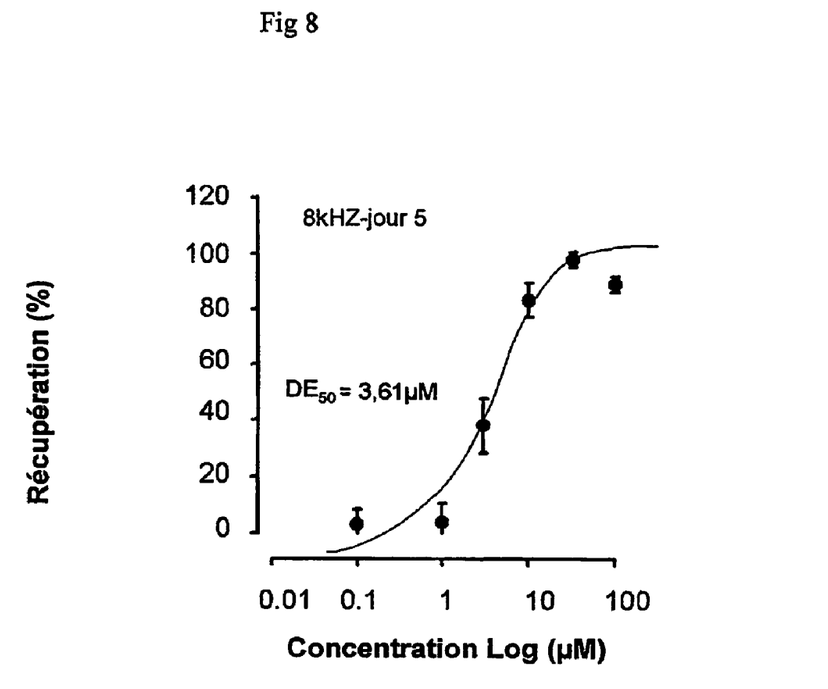
FIG. 8 depicts the determination of the effective dose of compound (1) allowing 50% recovery of hearing loss after trauma.

Five days after a traumatism of 120 dB for a duration of 30 min, the reading of the audiograms allows determination of the effective dose of compound (1) ($ED_{50}$=3.61 µM) allowing recovery of 50% of the hearing lost after the traumatism (FIG. 8).

Phase 2: Demonstration of the Protective Effect of Compound (1), Administered by Extracochlear Perfusion in a Post Treatment, Vis-à-Vis the Cell Loss Along the Cochlear Spiral and Hearing Loss. Determination of the Time in which, after a Traumatism, the Compound (1) Allows Recovery of 50% of Hearing.

Post Administration of Compound (1):

Preliminary studies have shown that a cochleostomy carried out after the exposure aggravates the traumatic effects of the sound. In this way, the animals implanted after the traumatism do not recover as well as the non-implanted animals. In order to eliminate the traumatism related to the cochleostomy, we have developed a non-traumatic method by applying the compound directly to the round window (extracochlear).

An osmotic minipump, is implanted under the skin and delivers the compound (1) into the cochlear via a catheter (extracochlear perfusion), 30 minutes or 1, 3, 6, 12 or 24 hours after the animals have undergone the sound traumatism.

This experiment is carried out on 30 animals.

The compound (1) is applied 48 hours before or 1, 3, 6, 12 or 24 hours after the traumatism in the middle ear (extracochlear perfusion) via an osmotic minipump (flow rate 1 µl/h, 200 µl volume, diffusion duration 7 days). This minipump is permanently implanted into the middle ear and diffuses the product directly onto the round window.

These experiments allow determination of the drug holiday of compound (1) (DH), i.e. the maximum time at which the compound (1) can be given after a traumatism while demonstrating a protective effect. The effective time allowing recovery of 50% of the lost hearing after the traumatism ($ET_{50}$) is also determined. This technique also allows determination, one month after the acoustic trauma, of the protective effect of compound (1), at a dose of 300 µM, vis-à-vis cell loss along the spiral cochlea caused by the traumatism.

Results Phase 2

Compound (1) at a concentration of 300 µM.

Functional Test: Audiogram.

Figure 9:
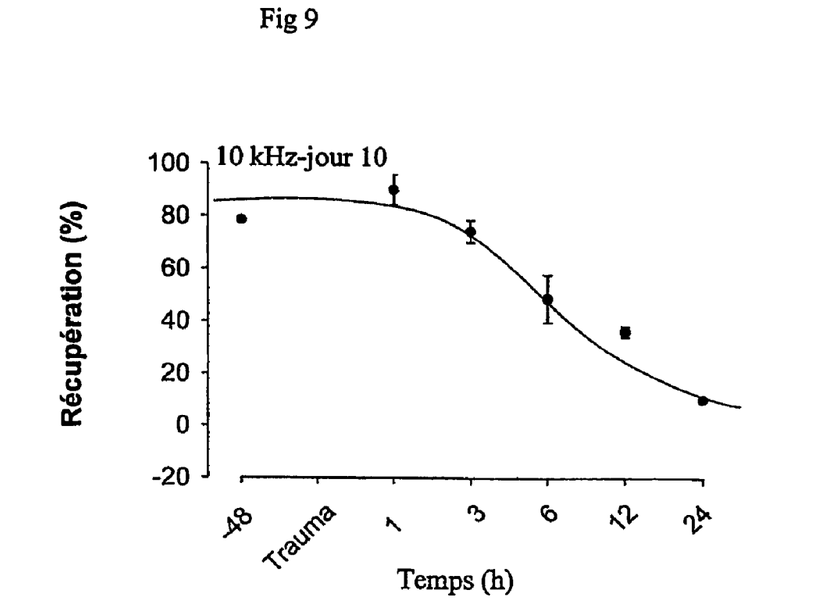
FIG. 9 depicts the percentage of recovery versus time from trauma after administration of compound (1).

One hour after the traumatism, the compound (1) preserves 90% of hearing. The time at which the compound (1) can be given after the traumatism while preserving 50% of hearing is determined as between 6 to 7 hours. The therapeutic window of the compound (1) is 24 hours after an acoustic traumatism of 120 dB for a duration of 30 minutes. This means that the compound (1) in this model is active in the first 24 hours after the acoustic trauma (cf. FIG. 9: audiograms carried out 10 days after a sound trauma).

Morphological Study: Histology of the Cells Along the Cochlear Spiral One Month after the Acoustic Traumatism.

The extracochlear perfusion of 300 µM of compound (1) started six hours after the acoustic trauma still protects a large part of the acoustic hair cells one month after the acoustic trauma. In fact only 32% of the internal acoustic hair cells and 18% of the external acoustic hair cells are absent in the area damaged by the acoustic trauma compared with the contralateral side which is exposed to the noise but not treated with the compound (1) where 86% of the internal acoustic hair cells and 62% of the external acoustic hair cells are absent in the area damaged by the acoustic trauma.

The invention claimed is:

1. A method of protecting acoustic hair cells comprising administering to a patient in need thereof a heterocyclic derivative of formula (I)

diastereoisomers of derivative (I), or combinations thereof,
wherein R is a ($C_1$-$C_6$) alkyl, aryl alkyl or —C(O)R' radicals;
wherein R' is a ($C_1$-$C_6$) alkyl or aralkyl radical;
the alkyl or aryl radicals being optionally substituted by one or more identical or different substituents including: ($C_1$-$C_6$) alkyl, hydroxy, ($C_1$-$C_6$) alkoxy, nitro, cyano, halogen or —$NR_1R_2$;
wherein $R_1$ and $R_2$ are independently, a hydrogen atom or an ($C_1$-$C_6$)alkyl radical.

2. The method of claim 1, wherein R is —C(O)R'.
3. The method of claim 2, wherein R' is an alkyl radical.
4. The method of claim 3, wherein R is —C(O)—$CH_3$.
5. The method of claim 1, wherein the derivative (I) has the formula ($I_A$)

6. The method of claim 1, wherein the derivative (I) has the formula ($I_{A1}$)

7. The method of claim 1, wherein the derivative (I) has the formula (I_A2)

8. The method of claim 1, wherein the derivative (I) has the formula (I_B)

9. The method of claim 1, wherein the derivative (I) has the formula (I_B1)

10. The method of claim 1, wherein the derivative (I) has the formula (I_B2)

11. The method of claim 1, wherein the derivative is administered following the administration of a medicament, wherein the medicament comprises antibiotics, anti-cancer drugs, non-steroidal anti-inflammatory agents, diuretics, antiulceratives, anticonvulsant agents, or combinations thereof.

12. The method of claim 11, wherein the medicament is an antibiotic.

13. The method of claim 12, wherein the antibiotic is gentamicin.

14. The method of claim 1, wherein said method protects acoustic hair cells following presbycusis.

15. The method of claim 1, further comprising administering at least one other substance with pharmaceutical activity which is able to treat hearing loss or to treat any pathologies associated with hearing loss.

16. The method of claim 15, wherein the other substance with pharmaceutical activity includes: antioxidants, calpain inhibitors, peripheral vasodilitators, agonists or antagonists of the NMDA receptor, peptide inhibitors of c-Jun N-terminal kinase or combinations thereof.

17. A method of treating hearing loss comprising administering, to a patient in need thereof up to 24 hours following an acoustic traumatism, a heterocyclic derivative of formula (I)

diastereoisomers of derivative (I), or combinations thereof, wherein R is a $(C_1-C_6)$ alkyl, aryl alkyl or —C(O)R' radical;

wherein R' is a $(C_1-C_6)$ alkyl or aralkyl radical;

the alkyl or aryl radicals being optionally substituted by one or more identical or different substituents including: $(C_1-C_6)$ alkyl, hydroxy, $(C_1-C_6)$ alkoxy, nitro, cyano, halogen or —$NR_1R_2$;

wherein $R_1$ and $R_2$ are independently, a hydrogen atom or an $(C_1-C_6)$alkyl radical.

18. The method of claim 17, wherein R is —C(O)R'.

19. The method of claim 18, wherein R' is an alkyl radical.

20. The method of claim 18, wherein R is —C(O)—$CH_3$.

21. The method of claim 17, wherein the derivative (I) has the formula (I_A)

22. The method of claim 17, wherein the derivative (I) has the formula (I_A1)

23. The method of claim 17, wherein the derivative (I) has the formula

(I<sub>A2</sub>)

24. The method of claim 17, wherein the derivative (I) has the formula

(I<sub>B</sub>)

25. The method of claim 17, wherein the derivative (I) has the formula (I<sub>B1</sub>)

26. The method of claim 17, wherein the derivative (I) has the formula (I<sub>B2</sub>)

27. The method of claim 17, wherein the derivative (I) is administered 12 hours following an acoustic traumatism.

28. The method of claim 17, wherein the derivative (I) is administered 7 hours following an acoustic traumatism.

29. The method of claim 1, wherein the derivative is administered following the administration of a medicament, wherein the medicament comprises antibiotics, anti-cancer drugs, non-steroidal anti-inflammatory agents, diuretics, antiulceratives, anticonvulsant agents, or combinations thereof.

30. The method of claim 29, wherein the antibiotic is gentamicin.

31. The method of claim 17, further comprising administering at least one other substance with pharmaceutical activity comprising antioxidants, calpain inhibitors, peripheral vasodilitators, agonists or antagonists of the NMDA receptor, peptide inhibitors of c-Jun N-terminal kinase or combinations thereof.

\* \* \* \* \*